(12) United States Patent
Zumbrum

(10) Patent No.: US 10,647,565 B2
(45) Date of Patent: May 12, 2020

(54) FLUID TRANSFER INTERFACE

(71) Applicant: ALLPURE TECHNOLOGIES, INC., New Oxford, PA (US)

(72) Inventor: Michael A. Zumbrum, New Oxford, PA (US)

(73) Assignee: Sartorius Stedium North America, Inc., Bohemia, NY (US)

(*) Notice: Subject to any disclaimer, the term of this patent is extended or adjusted under 35 U.S.C. 154(b) by 138 days.

(21) Appl. No.: 15/171,969

(22) Filed: Jun. 2, 2016

(65) Prior Publication Data
US 2016/0311674 A1    Oct. 27, 2016

Related U.S. Application Data

(63) Continuation of application No. PCT/US2013/073508, filed on Dec. 6, 2013.

(51) Int. Cl.
*B67D 7/02* (2010.01)
*B01L 3/00* (2006.01)
(Continued)

(52) U.S. Cl.
CPC .............. *B67D 7/0288* (2013.01); *A61J 1/10* (2013.01); *A61J 1/1412* (2013.01); *B01L 3/561* (2013.01);
(Continued)

(58) Field of Classification Search
CPC ........ B67D 7/0288; B67D 7/38; C12M 23/26; C12M 23/14; C12M 23/38; F16K 15/00;
(Continued)

(56) References Cited

U.S. PATENT DOCUMENTS 1,438,899 A    12/1922   Cassidy
1,577,539 A     3/1926   Alexander
(Continued)

FOREIGN PATENT DOCUMENTS

DE    3505492    8/1986
GB     781520    8/1957
(Continued)

OTHER PUBLICATIONS

"Saint-Gobain Biopharm C-Flex EZ Top container closures", http://www.biopharm.saint-gobain.com/en/products.asp?id=66; Oct. 15, 2013.
(Continued)

*Primary Examiner* — Jessica Cahill
*Assistant Examiner* — Patrick C Williams
(74) *Attorney, Agent, or Firm* — Womble Bond Dickinson (US) LLP

(57) ABSTRACT

Fluid transfer interfaces for transferring fluid into or out of vessels, namely flexible polymeric bags. The fluid transfer interfaces have a body for use in connection with a vessel, or combined therewith, one or more apertures extending through the body, and one or more fluid transfer conduits secured to the body by way of a cast seal and extending continuously and axially through the one or more apertures. Also disclosed is a vessel closure having one or more fluid transfer conduits extending through the closure, the fluid transfer conduits affixed to the closure by a cast seal.

21 Claims, 10 Drawing Sheets

(51) Int. Cl.
*A61J 1/10* (2006.01)
*A61J 1/14* (2006.01)
*B65D 47/06* (2006.01)
*B67D 7/38* (2010.01)
*C12M 1/00* (2006.01)
*F16K 7/04* (2006.01)
*F16K 15/00* (2006.01)

(52) U.S. Cl.
CPC ............ *B01L 3/563* (2013.01); *B65D 47/06* (2013.01); *B67D 7/38* (2013.01); *C12M 23/14* (2013.01); *C12M 23/26* (2013.01); *C12M 23/38* (2013.01); *F16K 7/04* (2013.01); *F16K 15/00* (2013.01); *B01L 3/505* (2013.01); *B01L 2200/0689* (2013.01)

(58) Field of Classification Search
CPC .......... F16K 7/04; B65D 47/06; A61J 1/1412; A61J 1/10; B01L 3/505; B01L 2200/0689; B01L 3/561; B01L 3/563
See application file for complete search history.

(56) References Cited

U.S. PATENT DOCUMENTS

| | | | |
|---|---|---|---|
| 1,834,085 A | 12/1931 | Bloom | |
| 2,186,908 A | 1/1940 | Page et al. | |
| 2,191,495 A | 2/1940 | Nesset | |
| 2,226,312 A | 12/1940 | Kuhns | |
| 2,439,572 A * | 4/1948 | Levin | C12M 23/08 422/419 |
| 2,744,661 A | 5/1956 | Davis | |
| 3,130,260 A | 4/1964 | Gray | |
| 3,276,447 A * | 10/1966 | Hamilton | A61B 5/15003 128/DIG. 24 |
| 3,354,012 A | 11/1967 | Forman et al. | |
| 3,360,008 A | 12/1967 | Papale et al. | |
| 3,458,619 A | 7/1969 | Prochaska | |
| 3,467,270 A | 9/1969 | Eady | |
| 3,499,568 A | 3/1970 | Riera | |
| 3,793,672 A | 2/1974 | Wetmore | |
| 3,794,333 A * | 2/1974 | Czernik | F16J 15/123 277/593 |
| 3,938,035 A | 2/1976 | Fletcher | |
| 4,032,311 A | 6/1977 | Bohmrich et al. | |
| 4,045,860 A | 9/1977 | Winckler | |
| 4,080,989 A | 3/1978 | Chapelsky | |
| 4,116,199 A | 9/1978 | Bryne | |
| 4,165,814 A | 8/1979 | Seel | |
| 4,174,743 A | 11/1979 | Beny | |
| 4,334,993 A | 6/1982 | Norton | |
| 4,335,717 A | 6/1982 | Bujan et al. | |
| 4,336,802 A | 6/1982 | Stone et al. | |
| 4,360,776 A * | 11/1982 | Bauman | G01R 33/60 324/316 |
| 4,396,016 A | 8/1983 | Becker | |
| 4,499,148 A | 2/1985 | Goodale | |
| 4,581,012 A | 4/1986 | Brown et al. | |
| 4,700,861 A | 10/1987 | Neward | |
| 4,701,159 A | 10/1987 | Brown et al. | |
| 4,715,359 A | 12/1987 | Ryo | |
| 4,784,299 A | 11/1988 | Stenger | |
| 4,785,974 A * | 11/1988 | Rudick | B67D 1/0002 141/114 |
| 4,863,030 A | 9/1989 | Bayer et al. | |
| 4,938,371 A | 7/1990 | Vercillo | |
| 4,993,573 A | 2/1991 | Freidel et al. | |
| 5,025,955 A | 6/1991 | Stenger | |
| 5,100,010 A | 3/1992 | Waters | |
| 5,114,045 A | 5/1992 | Herpe | |
| 5,245,955 A | 9/1993 | Husted | |
| 5,300,060 A | 4/1994 | Nelson | |
| 5,350,080 A | 9/1994 | Brown | |
| 5,358,872 A | 10/1994 | Mussi et al. | |
| 5,362,642 A | 11/1994 | Kern | |
| H1430 H | 4/1995 | Apel et al. | |
| 5,441,197 A | 8/1995 | Gellert et al. | |
| 5,492,531 A | 2/1996 | Post et al. | |
| 5,505,495 A | 4/1996 | Godeau | |
| 5,507,904 A * | 4/1996 | Fisher | A61J 1/10 156/252 |
| 5,522,155 A | 6/1996 | Jones | |
| 5,695,215 A | 12/1997 | Headley et al. | |
| 5,733,452 A | 3/1998 | Whitlock | |
| 5,988,422 A | 11/1999 | Vallot | |
| 6,039,718 A * | 3/2000 | Niedospial, Jr. | A61J 1/10 206/828 |
| 6,062,440 A | 5/2000 | Murray | |
| 6,071,005 A | 6/2000 | Ekambaram | |
| 6,095,356 A | 8/2000 | Rits | |
| 6,165,362 A | 12/2000 | Nohren, Jr. et al. | |
| 6,223,938 B1 | 5/2001 | Pare et al. | |
| 6,225,562 B1 | 5/2001 | Fujishita | |
| 6,290,265 B1 | 9/2001 | Warburton-Pitt et al. | |
| 6,334,888 B1 | 1/2002 | Collas et al. | |
| 6,340,033 B2 | 1/2002 | Paradis et al. | |
| 6,430,033 B1 | 1/2002 | Paradis | |
| 6,499,618 B1 | 12/2002 | Leclerc | |
| 6,520,505 B1 * | 2/2003 | Kogler | F16L 5/02 138/112 |
| 6,523,711 B1 | 2/2003 | Hughes | |
| 6,581,637 B2 | 6/2003 | Hamamoto | |
| 6,779,575 B1 | 8/2004 | Arthun | |
| 6,966,581 B2 | 11/2005 | Mastropaolo | |
| 6,994,699 B2 | 2/2006 | Houwaert | |
| 7,087,047 B2 | 8/2006 | Kraus et al. | |
| 7,093,859 B2 | 8/2006 | Warburton-Pitt et al. | |
| 7,140,404 B2 * | 11/2006 | Cupples | G01F 23/164 141/95 |
| 7,293,477 B2 | 11/2007 | Furey | |
| 7,306,583 B2 | 12/2007 | Goudaliez et al. | |
| 7,407,612 B2 | 8/2008 | Warburton-Pitt et al. | |
| 7,497,130 B2 | 3/2009 | Woods | |
| 7,500,949 B2 | 3/2009 | Gottlieb et al. | |
| 7,686,037 B2 | 3/2010 | Krywitsky | |
| 7,708,923 B1 | 5/2010 | Helicke et al. | |
| 7,784,630 B2 | 8/2010 | Walsh | |
| 7,874,467 B2 | 1/2011 | Pardes et al. | |
| 8,008,065 B2 | 8/2011 | Selker et al. | |
| 8,235,067 B2 | 8/2012 | Gagne et al. | |
| 8,342,737 B2 | 1/2013 | Greller et al. | |
| 8,505,396 B2 | 8/2013 | Zumbrum | |
| 8,505,586 B2 | 8/2013 | Zumbrum | |
| 8,524,174 B2 | 9/2013 | Levent | |
| 8,573,424 B2 | 11/2013 | Dubs | |
| 8,871,317 B2 | 10/2014 | Cai et al. | |
| 9,259,563 B2 | 2/2016 | Klingel, Jr. et al. | |
| 9,376,305 B2 | 6/2016 | Zumbrum | |
| 9,550,969 B2 | 1/2017 | Chotteau | |
| 2001/0015226 A1 | 8/2001 | Hamamoto et al. | |
| 2001/0017161 A1 | 8/2001 | Paradls et al. | |
| 2001/0035093 A1 | 11/2001 | Yokota | |
| 2002/0162648 A1 | 11/2002 | Crook | |
| 2002/0185186 A1 | 12/2002 | Juliar | |
| 2003/0052074 A1 | 3/2003 | Chang | |
| 2003/0208151 A1 | 11/2003 | Kraus et al. | |
| 2004/0064086 A1 | 4/2004 | Gottlieb et al. | |
| 2004/0260265 A1 | 12/2004 | Goudaliez et al. | |
| 2005/0067367 A1 | 3/2005 | Carballido | |
| 2005/0115917 A1 | 6/2005 | Odet | |
| 2005/0167390 A1 | 8/2005 | Dubs et al. | |
| 2006/0010991 A1 | 1/2006 | Woods et al. | |
| 2006/0086758 A1 | 4/2006 | Coles | |
| 2007/0193375 A1 | 8/2007 | Pandori et al. | |
| 2008/0087626 A1 | 4/2008 | Tsai | |
| 2008/0277926 A1 | 11/2008 | Inman, Sr. et al. | |
| 2008/0281200 A1 | 11/2008 | Voic et al. | |
| 2009/0049988 A1 * | 2/2009 | Meindl | B01D 53/228 95/285 |
| 2009/0090689 A1 | 4/2009 | Walsh | |
| 2009/0236374 A1 | 9/2009 | Pardes et al. | |
| 2010/0065305 A1 | 3/2010 | Bernauer | |
| 2010/0133459 A1 | 6/2010 | Zumbrum | |

(56) References Cited

U.S. PATENT DOCUMENTS

| | | |
|---|---|---|
| 2010/0164176 A1 | 7/2010 | Beele |
| 2010/0183251 A1 | 7/2010 | Neltner et al. |
| 2010/0288382 A1 | 11/2010 | Levent et al. |
| 2011/0018206 A1 | 1/2011 | Beele |
| 2011/0155274 A1 | 6/2011 | Zumbrum |
| 2012/0064274 A1 | 3/2012 | Cai et al. |
| 2014/0103077 A1 | 4/2014 | Zumbrum |
| 2014/0190570 A1 | 7/2014 | Zumbrum |
| 2016/0195208 A1 | 7/2016 | Cassiday et al. |
| 2016/0311674 A1 | 10/2016 | Zumbrum |

FOREIGN PATENT DOCUMENTS

| | | |
|---|---|---|
| JP | 2001031126 | 2/2001 |
| JP | 2007176537 | 7/2007 |
| JP | 4466778 | 5/2010 |
| KR | 200116728 | 4/1998 |
| WO | WO 9630274 | 10/1996 |
| WO | WO 2005084372 | 9/2005 |
| WO | WO 2010008396 | 1/2010 |
| WO | PCT/US2011/041462 | 6/2011 |
| WO | 2012177250 | 12/2012 |
| WO | PCT/US2013/073508 | 12/2013 |
| WO | 2015084388 | 6/2015 |
| WO | PCT/US2015/060159 | 11/2015 |

OTHER PUBLICATIONS

"Saint-Gobain Biopharm Sani-Tech EZ Top container closures", http://www.biopharm.saint-gobain.com/en/Products.asp?ID=31; Oct. 15, 2013.

European Patent Office, Supplementary European Search Report, EP11868058, dated Dec. 11, 2014.

GE Healthcare Life Sciences, "Disposable Cellbag bioreactors for WAVE Bioreactor systems", Data file 28-9511-36 AF, Jun. 2012, pp. 1-12, Sweden.

International Search Report, PCT/US2011/041462 dated Feb. 27, 2012.

Notification of Transmittal of the International Search Report and the Written Opinion of the International Searching Authority, PCT/2013/073508, dated Mar. 4, 2014.

Regarding related patents and patent applications, see the section of the accompanying IDS letter entitled "Related Patents and Patent Applications" for further information.

Extended European Search Report for EP13898703.7, dated Jul. 5, 2017, 8 pgs.

International Search Report and the Written Opinion of the International Searching Authority, PCT/US2015/060159, dated Aug. 11, 2016.

Sani-Tech EZ Top Container Closure, Saint-Gobain Performance Plastics, known at least as early as Jun. 6, 2011, 2 pgs.

EZ Top Container Closures, Saint-Gobain Performance Plastics, known at least as early as Jun. 6, 2011, 2 pgs.

Omnifit Solvent Safety Bottle Caps, Bio Chem Fluidics, known at least as early as Jun. 6, 2011, 16 pgs.

Injection-Molded Silicone Stoppers Platinum Cured, AdvantaPure, known at least as early as Jun. 6, 2011, 2 pgs.

BioClosure Systems Platinum Cured Silicone, AdvantaPure, known at least as early as Jun. 6, 2011, 4 pgs.

Disposable Polyethylene Vent Cap, Corning Life Sciences Catalot, http://catalog2.corning.com/LifeSciences/en-US/Shopping/ProductsDetails.aspx?pid . . . , known at least as early as Mar. 18, 2014, 2 pgs.

PTFE Faced Silicone Septa for GL25 Open Top PBT Screw Cap, Corning Life Sciences Catalog, http://catalog2.corning.com/LifeSciences/en-US/Shopping/ProductDetails.aspx?category . . . , known at least as early as Mar. 18, 2014, 1 pg.

"How it's made: Silicone Hoses manufacturing by Viper Performance" (ViperPerformanceUK) Oct. 1, 2014 (Oct. 1, 2014) [online] <url:https://www.youtube.com/watch?v=iuO0TdzHnWo> 5:30-6:30, 1 pg.

U.S. Appl. No. 14/128,259, filed Mar. 19, 2014, Vessel Closures and Methods for Using and Manufacturing Same, Michael A. Zumbrum.

U.S. Appl. No. 14/137,336, filed Dec. 20, 2013, Fluid Transfer Interface, Michael A. Zumbrum.

U.S. Appl. No. 15/171,947, filed Jun. 2, 2016, Fluid Transfer Interface, Michael A. Zumbrum.

U.S. Appl. No. 15/171,969, filed Jun. 2, 2016, Fluid Transfer Interface, Michael A. Zumbrum.

\* cited by examiner

FLUID TRANSFER INTERFACE

CROSS-REFERENCE TO RELATED APPLICATION

This application is a continuation of PCT Application Number PCT/US2013/073508, filed Dec. 6, 2013, which is incorporated herein by reference in its entirety.

TECHNICAL FIELD

This disclosure relates generally to an interface allowing for the transfer of fluids and, more specifically, to a fluid transfer interface for use in combination with a vessel, the fluid transfer interface having fluid transfer conduits extending continuously through a body thereby providing a continuous fluid pathway without the use of barbed or luer connections.

BACKGROUND

During certain manufacturing processes, vessels containing various fluids are used. Often it is necessary to transfer fluid into or out of a vessel during the process and do so in a manner that eliminates or substantially eliminates the possibility of leakage. In particular, the need to transfer fluid in such a manner often arises in the manufacturing and processing of pharmaceuticals, biopharmaceuticals, or other biotechnology applications where processes are conducted in vessels of varying shapes and sizes. The need for fluid transfer into and out of a vessel arises in other applications and industries as well, including but not limited to, the production of food, cosmetics, paint, chemicals, including hazardous chemicals, and the transfer and handling of semiconductor fluids.

Regardless of the industry, during transfers or sampling, the fluid should not leak. Leakage exposes the contents of the vessels to the environment, thereby compromising the substantially sterile conditions in which the fluid was kept. In addition, when making such transfers, it is desirable to keep the environment surrounding a vessel free from contamination by the contents of the vessel or a sample taken therefrom. It is often the case that, throughout the manufacturing process, there is a need to maintain fluid communication with the interior of the vessel by way of, for example, tubing extending through a fluid transfer interface from the exterior of the vessel into the interior of the vessel, or from the interior to the exterior. To accomplish a substantially aseptic and leak-free transfer, it is desirable to control the environment through which the fluid flows. For example, the pathway from a vessel to a sample container should be substantially aseptic along the entire pathway. Furthermore, it is desirable that the fluid transfer interface be safe for use, reliable, and of relatively low-cost construction.

It is also desirable to transfer fluid using a fluid transfer interface that is pre-sterilized and disposable. A pre-sterilized, disposable fluid transfer interface avoids the need for an operator to sterilize the interface for use. Further, certain sterilization processes can damage fluid transfer interfaces and render them useless before their first use.

Known fluid transfer interfaces that serve as vessel closures utilize connections that extend from the body of an interface and then terminate with barbed ends or luer fittings onto which additional tubing or other fluid pathways are connected. Fluid transfer interfaces incorporating such terminations are deficient because, in the case of barbed attachments, the tubing connected to the barb can pull free. In the case of luers, including locking luer connections, fluid can still leak out of the fluid pathway thereby contaminating the environment surrounding the vessel and compromising the sterility of the process.

Thus, what is needed is a fluid transfer interface with a body from which continuous fluid transfer conduits extend, whereby the conduits extend through and are secured to the body, and to which a fluid control device may be connected. What is further needed is a low cost, disposable fluid transfer interface that is connected to a vessel, for example, a bioreactor bag, and to which fluid control devices may be connected that creates a substantially aseptic fluid pathway into and out of the vessel that does not suffer from the shortcomings of a barbed or luer termination, or other means of joining fluid pathways.

SUMMARY

Briefly described, there is disclosed a fluid transfer interface for use with a vessel comprising a body, one or more apertures extending through the body, and one or more fluid transfer conduits secured to the body by way of a cast seal and extending continuously and axially through the one or more apertures. The fluid transfer conduits may be sealingly connected to the body by way of the cast seal.

In another embodiment, there is disclosed a vessel closure comprising one or more fluid transfer conduits extending through the closure, the fluid transfer conduits affixed to the closure by a cast seal.

Thus, fluid transfer interfaces are disclosed that possess distinct attributes and represent distinct improvements over the prior art. These and other aspects, features, and advantages of the fluid interfaces of this disclosure will be better understood and appreciated upon review of the detailed description set forth below when taken in conjunction with the accompanying drawing figures, described briefly below. According to common practice, the various features of the drawings may not be drawn to scale. Dimensions and relative sizes of various features and elements in the drawings may be shown enlarged or reduced to illustrate more clearly the embodiments of the invention.

DETAILED DESCRIPTION OF PREFERRED EMBODIMENTS

Certain exemplary embodiments of the present invention are described below and illustrated in the accompanying figures. The embodiments described are only for purposes of illustrating the present invention and should not be interpreted as limiting the scope of the invention, which, of course, is limited only by the claims below. Other embodiments of the invention, and certain modifications and improvements of the described embodiments, will occur to those skilled in the art, and all such alternate embodiments, modifications, and improvements are within the scope of the present invention.

Figure 1:
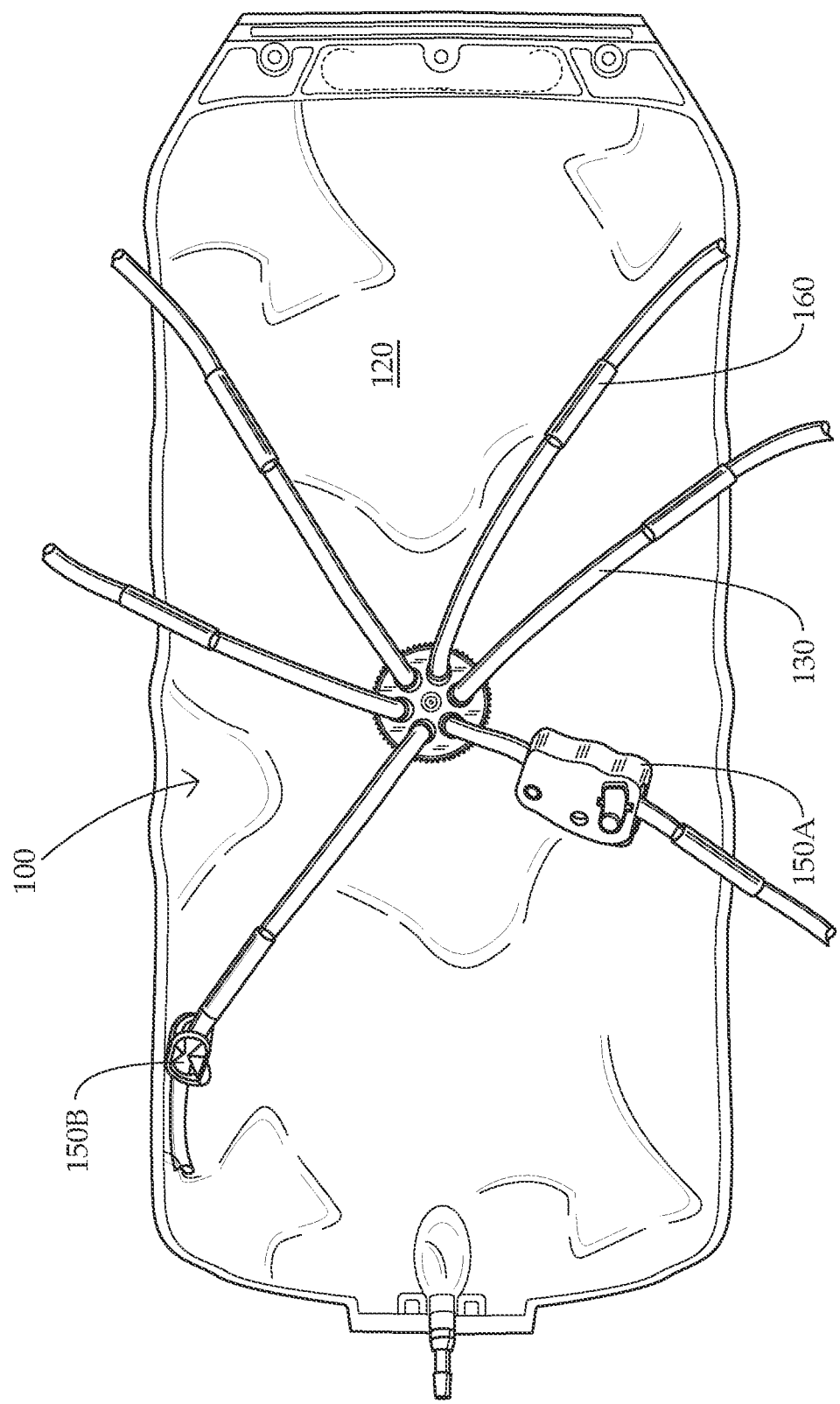
FIG. 1 is a top view of a fluid transfer interface connected to a vessel with several fluid transfer conduits and two fluid control devices.

Referring now in more detail to the drawing figures, wherein like reference numerals indicate like parts throughout the several views, FIG. 1 depicts a top view of an exemplary fluid transfer interface, in this case a fluid transfer interface with a body is combined for use with a vessel comprising a flexible polymeric container, often referred to as a bioreactor bag. Multiple apertures extend through the body and multiple fluid transfer conduits are secured to the body by way of a cast seal (not visible in FIG. 1) and extending continuously and axially through the one or more apertures. The body may be combined with a vessel by way of threaded connection, a clamp connection, a welded connection, a bonded connection, or by other mechanical means. Alternatively, the body may be formed as a singular unit with the vessel. For example, a bioreactor bag may be formed in a manner whereby the body is formed as an integral component of the bag when the bag is manufactured. Regardless of whether the body is a separate component, or formed as an integral part of the vessel, the body is combined with the vessel to form a leak-free connection.

It should be understood that the fluid transfer interface is not limited to use with any particular fluids but, depending on the size and composition of the interface and its constituent fluid transfer conduits, may be used with fluids with particulates or having a high viscosity or with fluids having no or very little particulate content or low viscosity.

The fluid transfer interface 100 illustrated in FIG. 1 generally depicts a body 110, discussed in more detail below, for use in combination with a vessel 120, where the body has one or more apertures extending axially through the body, fluid transfer conduits 130 extending axially through each aperture, and a cast seal 140 (not shown) disposed within the body and surrounding each conduit. The fluid transfer interface is not limited to the number fluid transfer conduits shown in FIG. 1, but may incorporate more or fewer conduits. The fluid transfer interface is suitable for use with vessels that include without limitation: containers, beakers, bottles, canisters, flasks, bags, receptacles, tanks, vats, vials, tubes, and the like that are generally used to contain fluids, slurries, and other similar substances. In a preferred embodiment, the fluid transfer interface has a body comprising a cap that is combined with a bag, as shown in FIG. 1, by way of a threaded connection.

In the fluid transfer interface illustrated in FIG. 1, the body is a cap. Suitable caps for the vessel closure include those commonly used in the field of pharmaceutical, biopharmaceutical, and biotechnology processing. Such caps include: a 38-430 cap with an outer diameter at the open end of approximately 42 mm and being approximately 29 mm tall; a centrifuge cap having an outer diameter at the open end of approximately 34 mm and being approximately 13 mm tall; a 20-415 cap with an outer diameter at the open end of approximately 24 mm and being approximately 14.6 mm tall; a GL-45 cap having an outer diameter at the open end of approximately 53.7 mm and being approximately 25.5 mm tall, bung ports, 53B caps, and 83B caps. The invention, however, is not limited to a cap of any particular dimensions.

Bodies of the fluid transfer interface may be made from thermoplastics such as polyolefins, polypropylene, polyethylene, polysulfone, polyester, polycarbonate, and glass filled thermoplastics. The invention, however, is not limited to a body made from any particular material(s). The bodies may also be made from thermosets such as epoxies, pheonolics, and novolacs. The body may also be a hygienic or sanitary clamp having dimensions disclosed in ASME BPE table DT-5-2 ("Hygienic Clamp Ferrule Standard Dimensions and Tolerances") (2009), which is incorporated by reference herein in its entirety. The body is not limited to caps or hygienic clamps but may constitute any suitable closure that seals the interior of a vessel from the exterior environment.

Also shown in FIG. 1 are two fluid control devices, 150A and 150B. Fluid control devices, such as but not limited to clamps and pinch valves, may be connected to the fluid transfer conduits and used to control the flow of fluid into or out of a vessel. In FIG. 1, the fluid control devices shown are two pinch clamps. Pinch clamp 150A is a Pure-Fit® TC tube clamp from Saint-Gobain Performance Plastics. Pinch clamp 150B is Clamp No. 13612 from Qosina Corporation. The pinch clamps shown are exemplary, and any type or variety of fluid control device may be utilized on the fluid transfer conduits.

Again returning to FIG. 1, sleeve 160 is shown. Sleeve 160 may be a deformable sleeve such as those disclosed and claimed in U.S. Pat. No. 8,505,586, which is incorporated by reference herein in its entirety and owned by the assignee of the instant application. In an embodiment, the deformable sleeve surrounds and is adhesively attached to flexible tubing. The deformable sleeve is attached to the flexible tubing at a location that facilitates substantially sealing, cutting, and detaching the deformable sleeve. In such embodiments, the sleeved is formed of a material having plasticity such that pressure applied to the sleeve causes the sleeve to deform about and seal the flexible tubing and upon continued application of pressure to the sleeve, the sleeve and flexible tubing are cut and the sleeve retains a deformed shape, thereby substantially sealing the tubing. In these embodiments, the flexible tubing is thermoplastic tubing, elastomeric tubing, or a combination of thermoplastic and elastomeric tubing.

Figure 2:
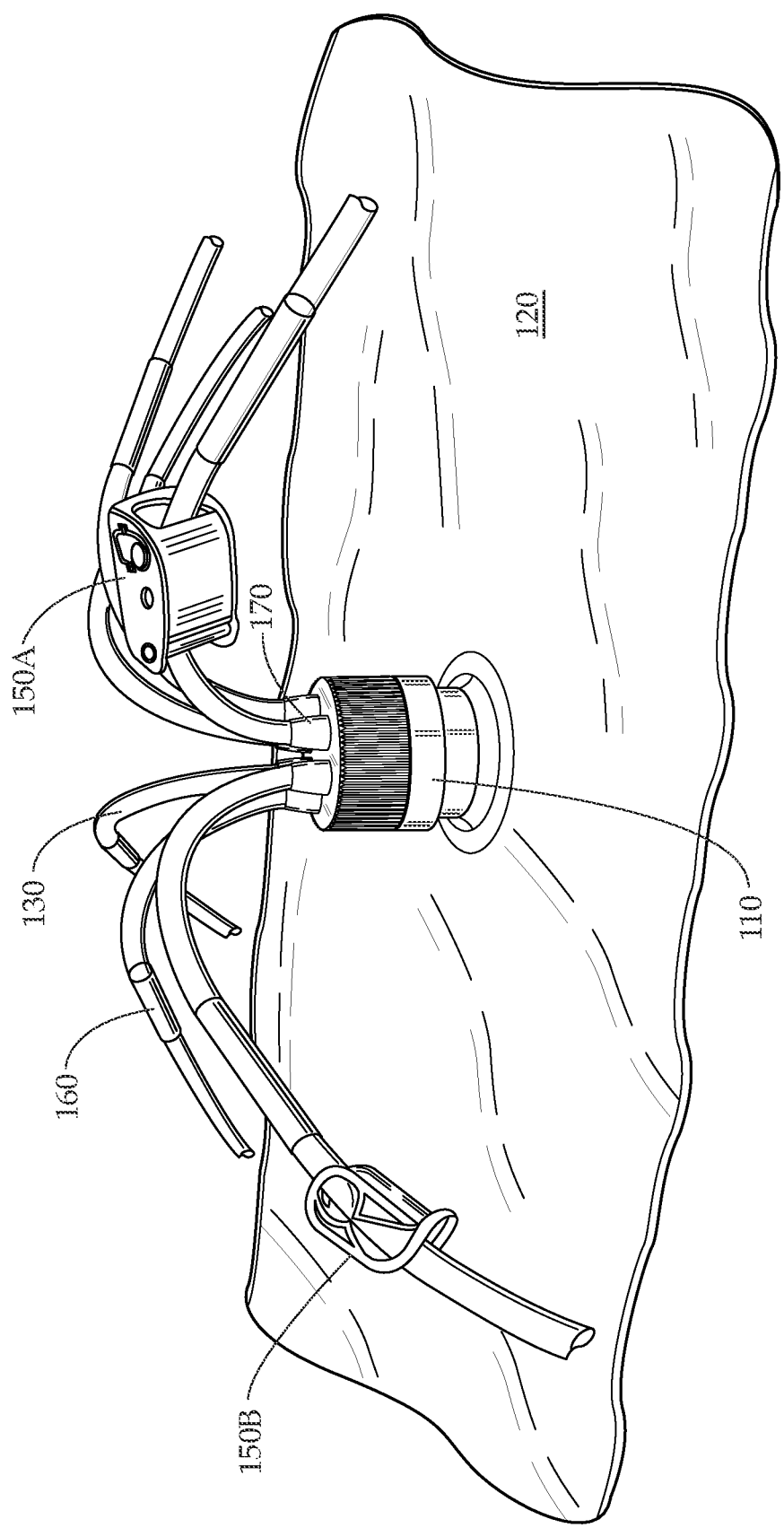
FIG. 2 is a perspective view of a fluid transfer interface connected to a vessel with several fluid transfer conduits and fluid control devices.
Figure 3:
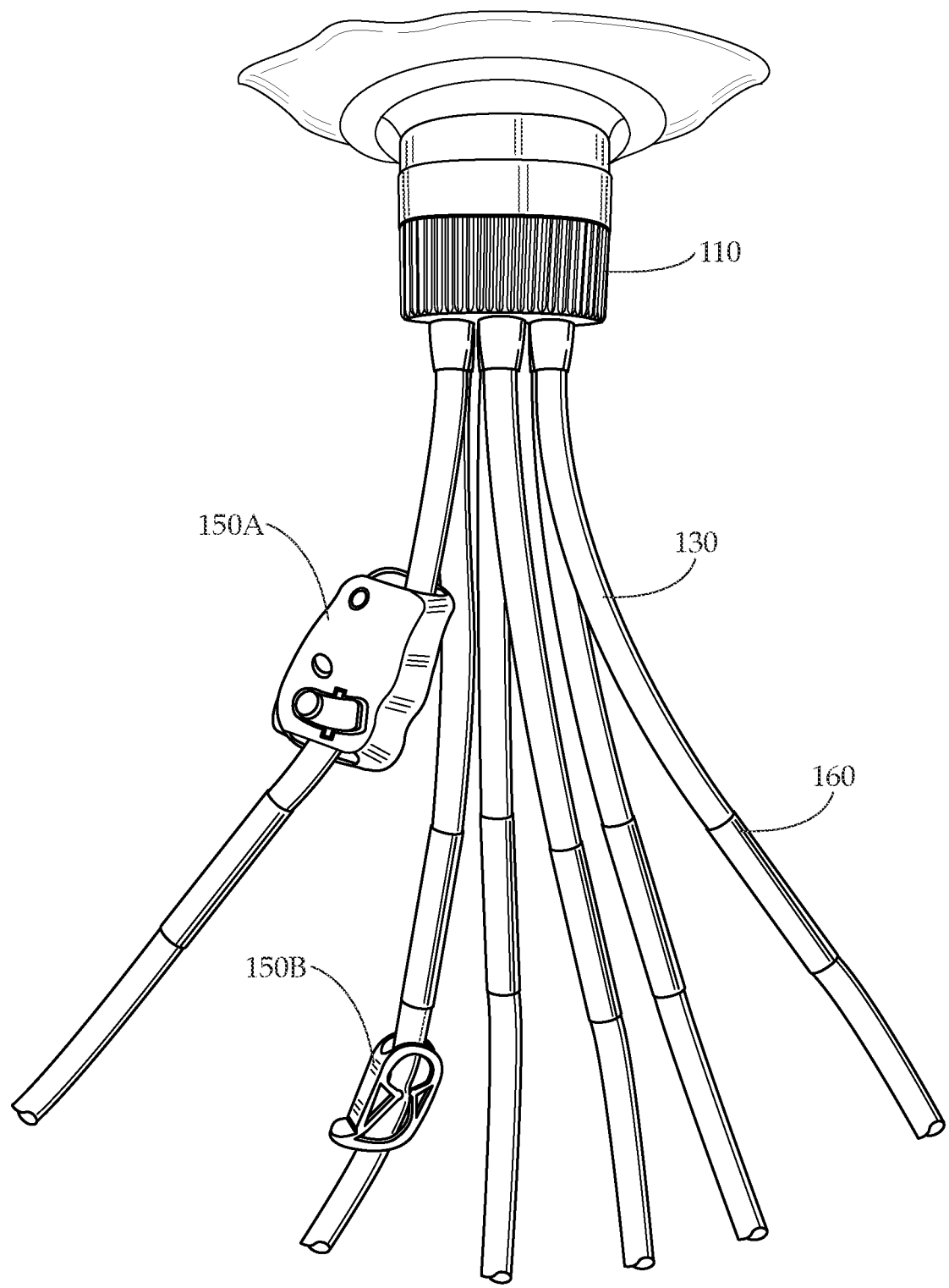
FIG. 3 is side view of a fluid transfer interface connected to a vessel with several fluid transfer conduits and fluid control devices.

Referring now to FIG. 2, a perspective view of a fluid transfer interface shows the body 110, the vessel 120, the inserts 130, optional fluid control devices 150A and 150B, and the optional sleeves 160. FIG. 3 depicts a side view of a fluid transfer interface, the body 110 (in connection with a vessel), the inserts 130, optional fluid control devices 150A and 150B, and optional sleeves 160.

Figure 4:
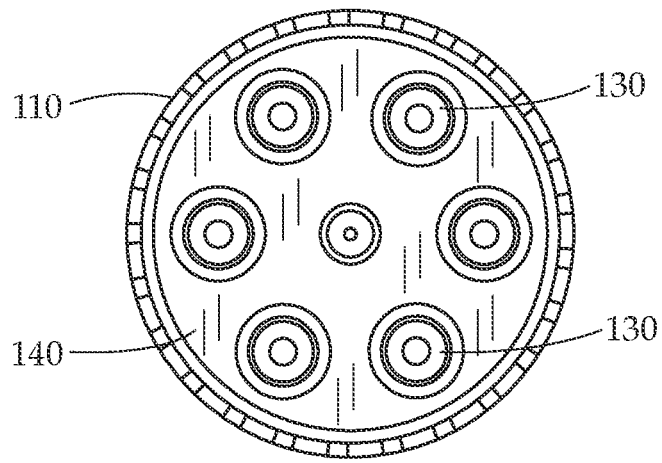
FIG. 4 is a bottom view of a fluid transfer interface showing several conduits and a cast seal.

FIG. 4 depicts a bottom view of a body 110, fluid transfer conduits 130, and a cast seal 140. The cast seal surrounds and secures the fluid transfer conduits to the body of the fluid transfer interface. Utilizing a cast seal provides for integration of continuous fluid transfer conduits from within a vessel to a point exterior of the vessel thereby providing a continuous fluid pathway without the use of connections, such as barbed or luer connections. In a preferred embodiment the cast seal is constructed from a self-leveling, pourable silicone such as room-temperature-vulcanizing ("RTV") silicone. The RTV silicone may be a two-component system (base plus curative) ranging in hardness from relatively soft to a medium hardness, such as from approximately 9 Shore A to approximately 56 Shore A. Suitable RTV silicones include Wacker® Elastocil® RT 622, a pourable, addition-cured two-component silicone rubber that vulcanizes at room temperature (available from Wacker Chemie AG), and Rhodorsil® RTV 1556, a two-component, high strength, addition-cured, room temperature or heat vulcanized silicone rubber compound (available from Blue Star Silicones). Both the Wacker® Elastocil® RT 622 and the Bluestar Silicones Rhodorsil® RTV 1556 have a viscosity of approximately 12,000 cP (mPa·s). The aforementioned silicones and their equivalents offer low viscosity, high tear cut resistance, high temperature and chemical resistance, excellent flexibility, low shrinkage, and the ability to cure a cast silicone seal at temperatures as low as approximately 24° C. (75° F.). The cast seal may also be constructed from dimethyl silicone or low temperature diphenyl silicone or methyl phenyl silicone. An example of phenyl silicone is Nusil MED 6010. Phenyl silicones are particularly appropriate for cryogenic applications. In another embodiment, the casting agent is a perfluoropolyether liquid. A preferred perfluoropolyether liquid is Sifel 2167, available from Shin-Etsu Chemical Co., Ltd. of Tokyo, Japan.

In an embodiment, the cast seal is disposed within the body of the vessel closure so that when the body is connected to or integrally combined into a vessel, such as a bioreactor bag, the cast seal creates an aseptic seal between the interior of the bag and the exterior of the bag, thereby protecting the environment and maintaining a closed and hygienic system. Preferably, the seal formed by the fluid transfer conduit between the interior of the vessel and the exterior environment is substantially aseptic. As best shown in FIG. 4, the cast seal 140 surrounds the fluid transfer conduits 130, thereby creating a seal and insert subassembly. In an embodiment, the seal between the cast seal 140 and insert 130 is substantially aseptic.

In one embodiment, the inserts are silicone tubing. For clarity, only a portion of the silicone tubing is shown in FIG. 1. The tubing may be of any length suitable and necessary for the desired process. In an embodiment, at least a portion of the silicone tubing is treated with a primer where the cast silicone surrounds the tubing. Suitable primers are SS-4155 available from Momentive™, Med-162 available from NuSil Technology, and Rodorsil® V-06C available from Bluestar Silicones of Lyon, France.

In another embodiment, the cast seal 140 is connected to the body by way of priming at least a portion of the body and adhesively attaching the cast seal to the body. In this embodiment, the cast seal will not pull away from the interior of the body.

The fluid transfer conduit may be constructed of a thermoset or a thermoplastic. If a thermoset is used, silicones, polyurethanes, fluoroelastomers or perfluoropolyethers are preferred construction materials for the conduits. If a thermoplastic is used, C-Flex® tubing, block copolymers of styrene-ethylene-butylene-styrene, PureWeld, PVC, polyolefins, or polyethylene are preferred construction materials. Multiple conduits may be used including combinations of thermoset and thermoplastic materials in the same fluid transfer interface.

When anchors (shown in FIGS. 5 and 6, discussed below) partially or completely surround each insert, the seal need not be constructed of cast silicone but may be made of any casting agent capable of bonding to the anchor. For example, in applications involving solvents, a casting agent such as perfluoropolyether liquid potting material could be used. Primers can be used to enhance bonding to the anchor and or body.

Figure 5:
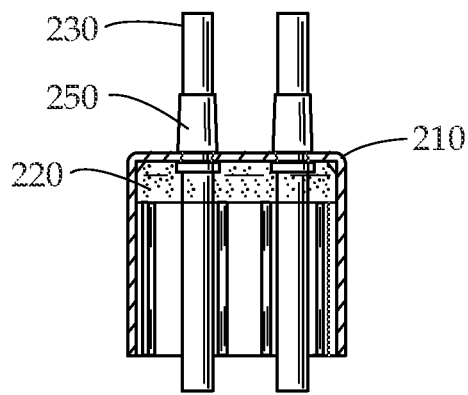
FIG. 5 is a cross-section of a fluid transfer interface body depicting two fluid transfer conduits, anchors, and a cast seal.

FIG. 5 depicts yet another embodiment of a body 210, a cast seal 220, fluid transfer conduits 230, and anchors 250. Fluid transfer conduits 230 may be, for example, silicone tubing, and the anchors 250 are constructed with a retaining nut portion in the interior of the body 210 and a conical section on the exterior of the body 210, thereby securing the fluid transfer conduits 230 to the body 210 by way of, for example, a friction fit.

Figure 6:
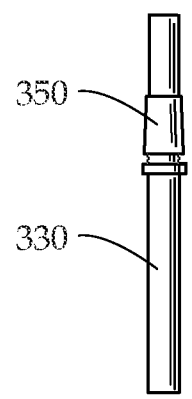
FIG. 6 is a side view of a fluid transfer conduit and an anchor.

FIG. 6 illustrates a fluid transfer conduit 330 and an anchor 350. The anchor 350 is the same anchor as depicted in FIG. 5 and illustrates how the anchor may be friction fit into an aperture in the body 210 by pressing the conical section into and through an aperture until the anchor is secured to the body.

Figure 7:
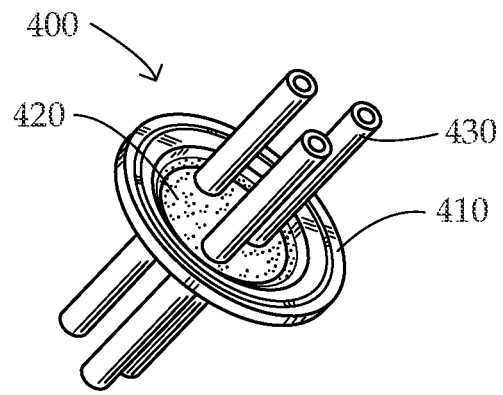
FIG. 7 is a perspective view of a fluid transfer interface body (a tri-clamp closure), three fluid conduits, and a cast seal.

FIG. 7 depicts fluid transfer interface 400 comprising a body 410, in this embodiment, a tri-clamp vessel closure, a cast seal 420, and fluid transfer conduits 430.

The fluid transfer conduits extending from the fluid transfer interface may be connected to a variety of vessels for collection of a sample. Acceptable vessels include, without limitation, bags, bottles, syringes, centrifuge tubes, or tubing. A plug may also be inserted in the end of the fluid transfer conduits. The fluid transfer conduits may also be connected to additional fluid control devices. For example, the terminal of a fluid transfer conduit may be welded to a manifold that provides for additional fluid pathways. An acceptable manifold is the Bio-Simplex™ manifold system available from J & J Scientific Products, Inc.

Figure 8:
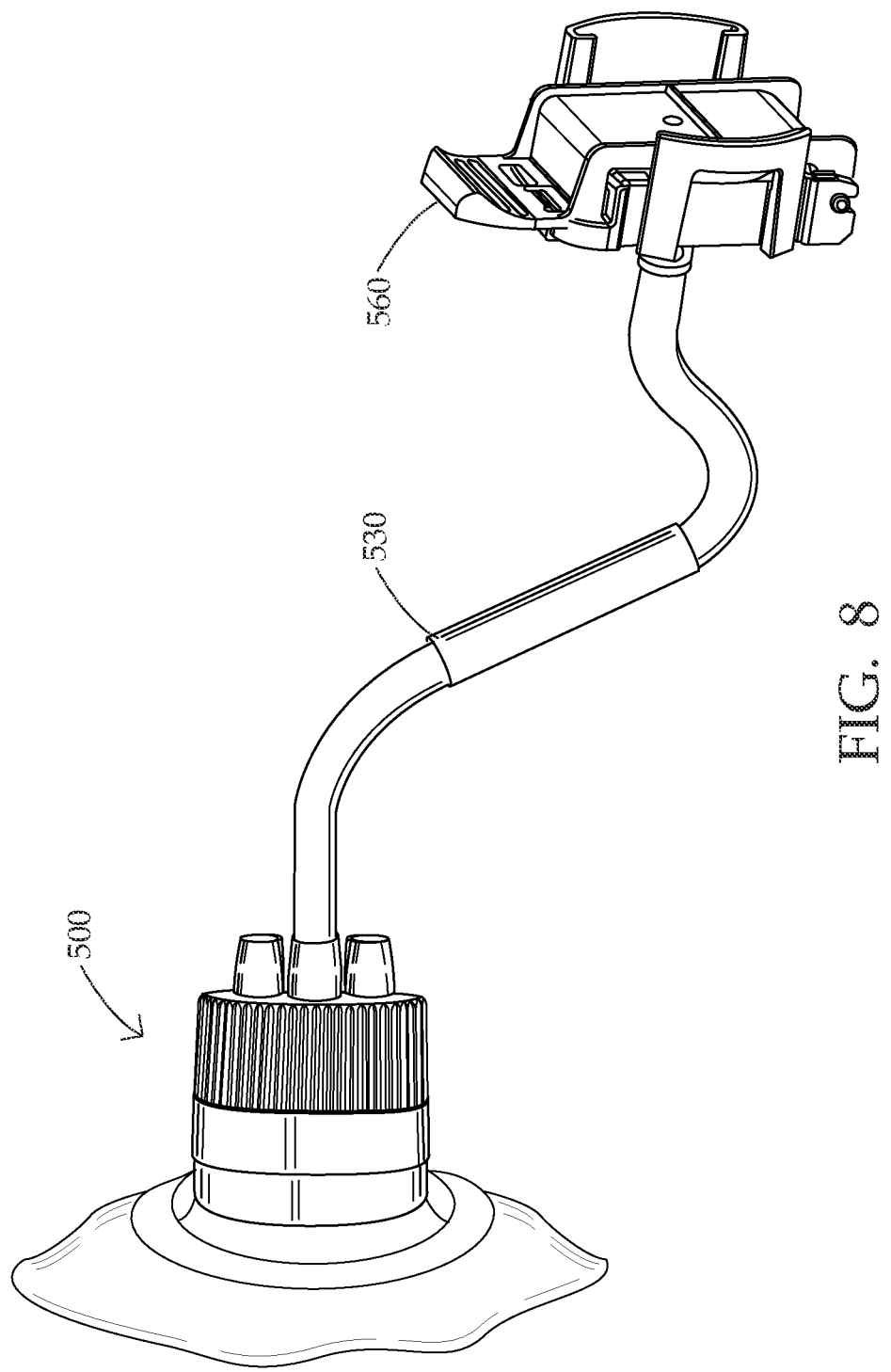
FIG. 8 is a perspective view of a fluid transfer interface wherein one fluid transfer conduit is connected to an AseptiQuik® connector.
Figure 9:
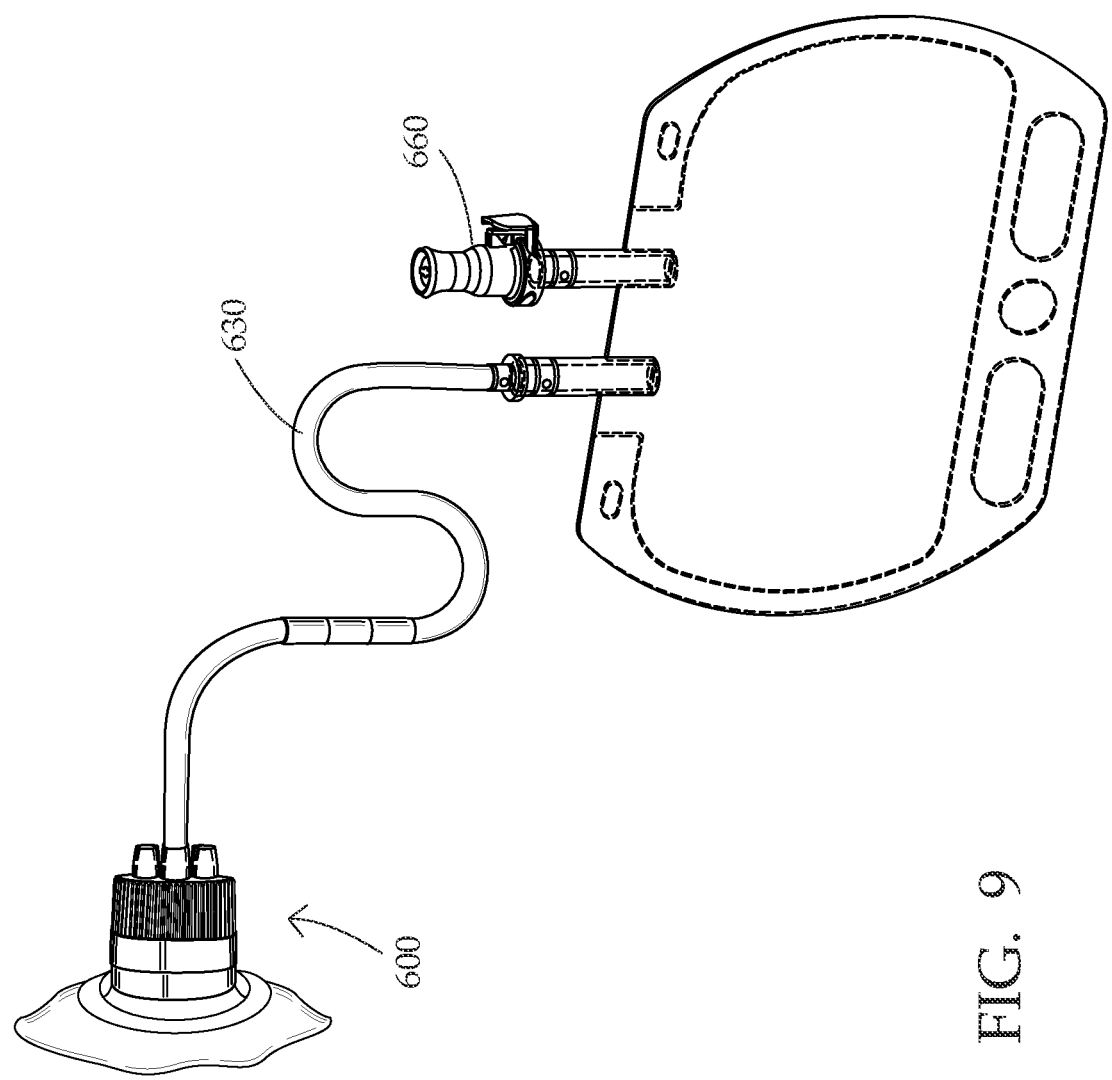
FIG. 9 is a perspective view of a fluid transfer interface wherein one fluid transfer conduit is connected to a sample bag to which is fitted a quick connect fitting.
Figure 10:
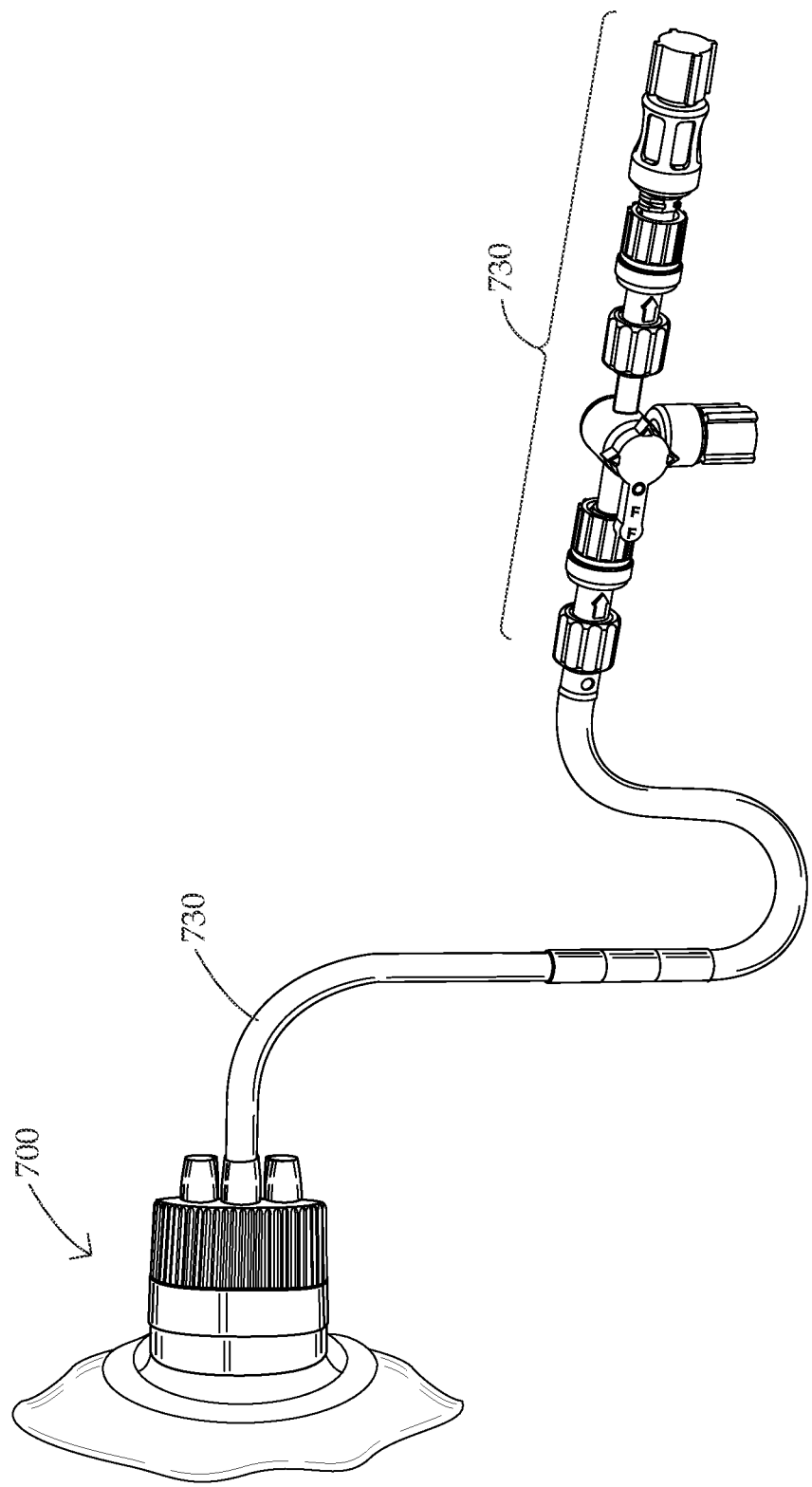
FIG. 10 is a perspective view of a fluid transfer interface wherein one fluid transfer conduit is connected to a BENCHMARK™ fitting.
Figure 11:
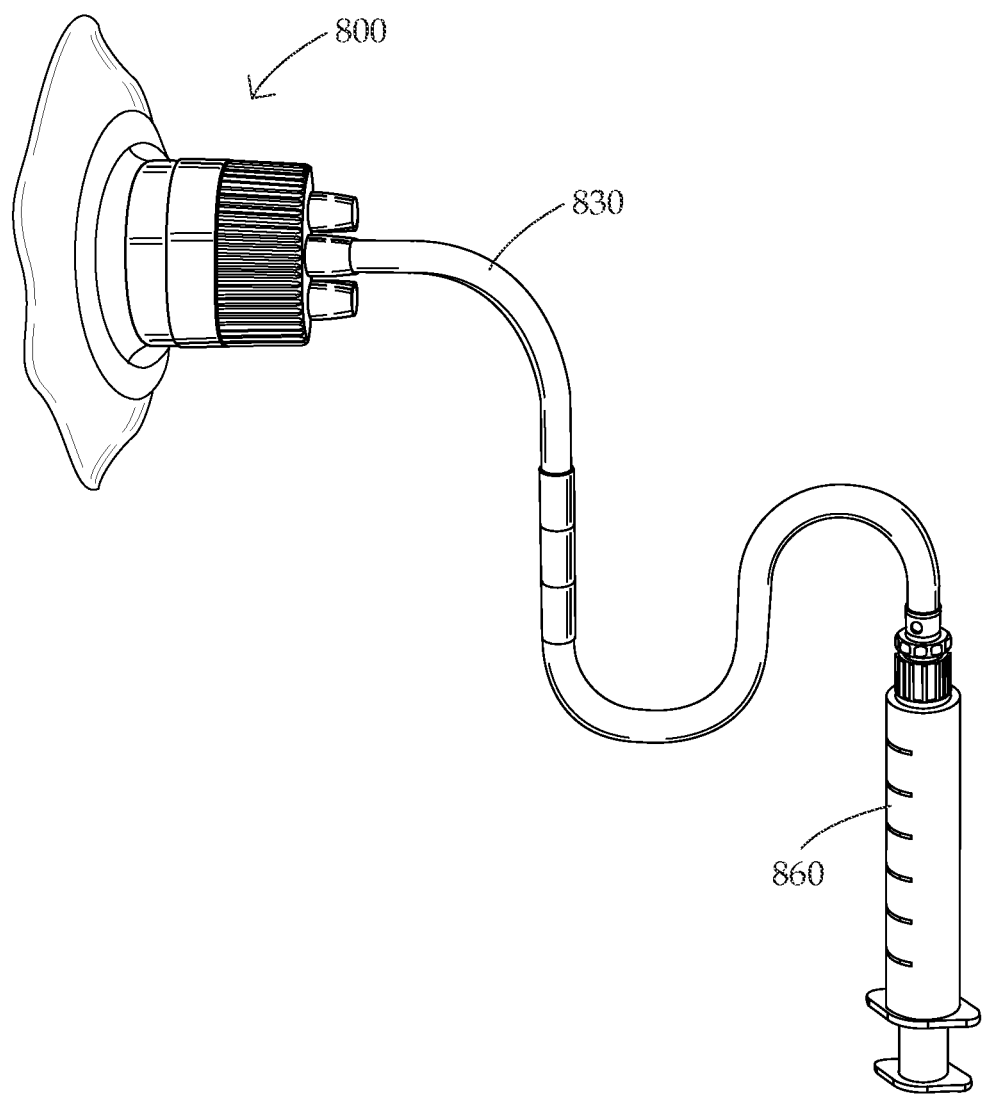
FIG. 11 is a perspective view of a fluid transfer interface wherein one fluid transfer conduit is connected to a syringe.
Figure 12:
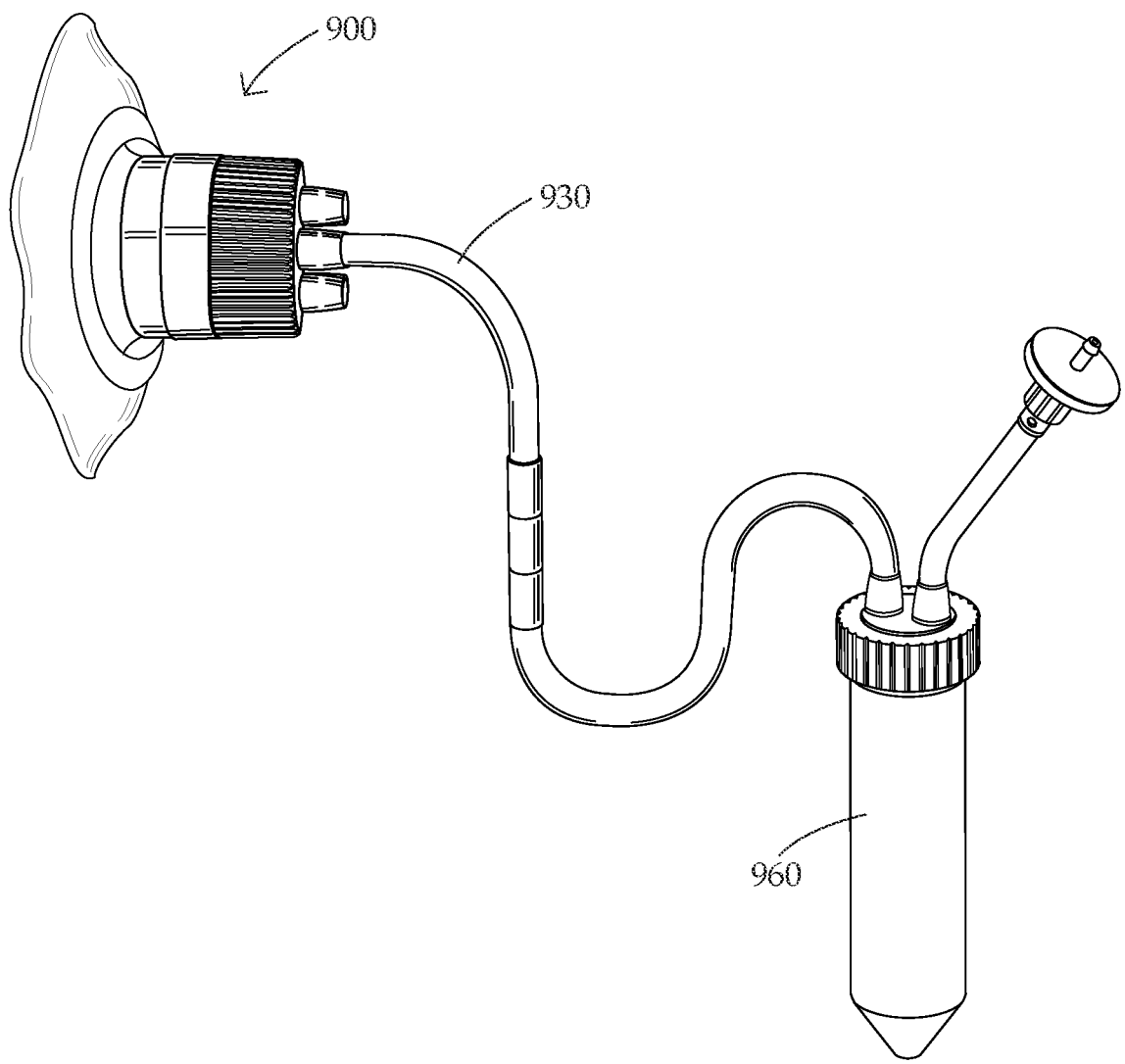
FIG. 12 is a perspective view of a fluid transfer interface wherein one fluid transfer conduit is connected to a centrifuge tube.
Figure 13:
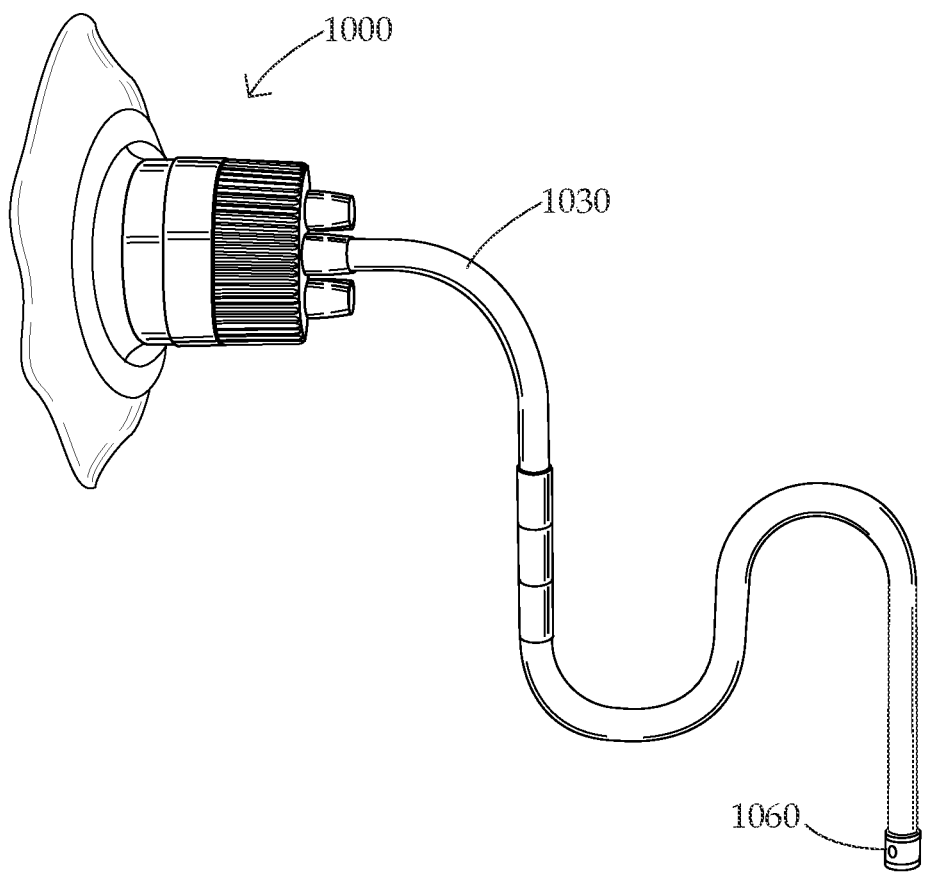
FIG. 13 is a perspective view of a fluid transfer interface wherein one fluid transfer conduit is connected to a plug.

Provided herewith are several depictions showing various potential embodiments of the fluid transfer device described herein. FIG. 8 depicts a fluid transfer interface 500 wherein one fluid transfer conduit 530 is connected to an AseptiQuik® connector 560 from Colder Products Company. FIG. 9 depicts a fluid transfer interface 600 wherein one fluid transfer conduit 630 is connected to a sample bag 670, to which is connected a standard quick connect fitting 660. FIG. 10 depicts a fluid transfer interface 700 wherein one fluid transfer conduit 730 is connected to a BENCHMARK™ fitting 760. FIG. 11 depicts a fluid transfer interface 800 wherein one fluid transfer conduit 830 is connected to a syringe 860. FIG. 12 depicts a fluid transfer interface 900 wherein one fluid transfer conduit 930 is connected to a centrifuge tube 960. FIG. 13 depicts a fluid transfer device 1000 wherein one fluid transfer conduit 1030 is connected to a plug 1060.

The fluid transfer interfaces disclosed herein may be manufactured by creating one or more apertures in a body. In an embodiment, the apertures may be made using a punch press. However, the apertures may be made using a drill, mill, laser, or any combination thereof. In another embodiment, the apertures are molded when the bodies are molded. Inserts are then inserted axially through the one or more apertures in the body. A casting agent is then cast into the interior of the body. The casting agent is then cured to form a seal around and bond to the one or more inserts. Preferred casting agents include liquid silicone and liquid perfluoropolyether.

In an alternative embodiment, a fluid transfer interface comprising one or more apertures through a body with tubing extending through the one more apertures may be manufactured by first creating a body with one or more apertures. The apertures in the body may be made by the methods mentioned above. Silicone tubing is then inserted through at least one aperture. Thermoplastic tubing is then inserted through at least one other aperture so that the fluid transfer interface has both silicone and thermoplastic tubing. A portion of the thermoplastic tubing is surrounded by a sleeve adhesively attached to the thermoplastic tubing. The sleeve is constructed of material capable of bonding with a casting agent. A casting agent is then cast into the body. The casting agent is cured to form a seal around and bond to the at least one sleeve surrounding at least a portion of the thermoplastic tubing and to the silicone tubing. In an embodiment, the thermoplastic tubing is C-Flex® tubing. Preferred casting agents include liquid silicone and liquid perfluoropolyether.

In the aforementioned methods for manufacturing fluid transfer interfaces, the liquid silicone may be cast at temperatures much lower than required for insert and/or injection molding. Accordingly, components may be incorporated into the fluid transfer interfaces described herein that could not be incorporated into fluid transfer interfaces manufactured using insert and/or injection molding. Such inserts include, but are not limited to, thermoplastic inserts such as C-Flex® tubing. Accordingly, the fluid transfer interfaces may combine elastomeric and thermoplastic tubing within the same interface. The fluid transfer interfaces also allow for a variety of different inserts to be included in a single interface, such as a variety of fittings, inserts, silicone tubing, C-Flex® tubing, temperature gauges, pH sensors, and others.

The fluid transfer interfaces disclosed herein are low cost and disposable but still capable of effectuating a substantially aseptic seal to a vessel while still allowing maximum flexibility in fluid transfer conduits and inserts and sensors. In addition, the methods of utilizing the fluid transfer interfaces described herein to circulate fluid into and out of a vessel provides a system of relatively few components all while maintaining a substantially aseptic system in which the fluid is located.

The fluid transfer interfaces disclosed herein may be assembled and then the entire devices or components thereof may be rendered substantially aseptic by, for example, gamma radiation. Alternatively, the entire devices or components thereof may be rendered substantially aseptic by exposure to steam above 121° C. for a period of time long enough to eliminate microorganisms. The entire devices or components thereof may also be rendered aseptic by chemical treatment, such as with ethylene oxide (ETO). Once rendered substantially aseptic, the fluid transfer interfaces may be appropriately packaged and stored to maintain the substantially aseptic state until ready for use.

The aforementioned fluid transfer interfaces are particularly useful when the vessel is a bioreactor bag. Such fluid transfer interfaces, combined with a bioreactor bag, may be used in single-use bioreactors, such as the Biostat® STR available from Sartorius. Fluid transfer conduits may be sized to accommodate high density cell culture applications and provide a sterile, low-cost manner of collecting samples from bioreactor bags without the risk of leakage found in prior art applications. As discussed above, the fluid transfer interface may be connected to a variety of sample vessels or additional fluid transfer devices.

The primary vessel (such as the bioreactor bag), the fluid transfer interface connected thereto, the fluid transfer conduits, and any sampling vessels or additional fluid transfer conduits, fittings, manifolds, or the like may be rendered substantially aseptic by the methods described above or others known in the art. Once rendered aseptic, the entire device may be aseptically packaged and distributed for use. The end user may open and utilize a completely closed and substantially aseptic system without risk of leaks due to the barbed or luer connectors extending from a bioreactor vessel.

The foregoing descriptions of fluid transfer interfaces, methods of manufacturing fluid transfer interfaces, and methods of utilizing fluid transfer interfaces illustrate and describe various embodiments. As various changes can be made in the above embodiments without departing from the scope of the invention disclosed and claimed herein, it is intended that all matter contained in the above description or shown in the accompanying figures shall be interpreted as illustrative and not limiting. Furthermore, the scope of the invention covers various modifications, combinations, alterations, etc., of the above-described embodiments that all are within the scope of the claims. Additionally, the disclosure shows and describes only selected embodiments of the invention, but the invention is capable of use in various other combinations, modifications, and environments and is capable of changes or modifications within the scope of the inventive concept as expressed herein, commensurate with the above teachings, and/or within the skill or knowledge of artisans in the relevant art. Furthermore, certain features and characteristics of each embodiment may be selectively interchanged and applied to other illustrated and non-illustrated embodiments of the invention without departing from the scope of the invention.

The invention claimed is:

1. An assembly, comprising:
a vessel having an interior and an exterior; and
a fluid transfer interface, comprising:
   a rigid body,
   one or more apertures extending through the body, and
   one or more fluid transfer conduits secured to the body by way of a cast seal and extending continuously and axially through the one or more apertures,
   the cast seal comprising a silicone casting agent disposed within the body in liquid form and cured into a cured state after the one or more fluid transfer conduits are inserted through the one or more apertures to permanently fix the cast seal to the body and permanently fix the cast seal to the one or more fluid transfer conduits;
   wherein the cast seal of the fluid transfer interface forms an aseptic seal between the interior of the vessel and the exterior of the vessel.

2. The assembly of claim 1, further comprising a fluid control device connected to the one or more fluid transfer conduits.

3. The assembly of claim 2 wherein the fluid control device is selected from the group consisting of a pinch valve, check valve, clamp, and plug.

4. The assembly of claim 2 further comprising a sensor extending through one of the apertures in the body.

5. The assembly of claim 2 wherein the fluid control device is a deformable sleeve.

6. The assembly of claim 5 wherein the deformable sleeve comprises a sleeve adhesively attached to and surrounding a portion of the flexible tubing.

7. The assembly of claim 1, wherein the vessel is a flexible container.

8. The assembly of claim 7, wherein the flexible container is a polymeric bag.

9. The assembly of claim 1, wherein the silicone is selected from the group consisting of dimethyl silicone, methyl phenyl silicone, and diphenyl silicone.

10. The assembly of claim 1 wherein the body is threadedly connected to the vessel.

11. The assembly of claim 1 wherein the body is mechanically connected to the vessel.

12. The assembly of claim 11 wherein the mechanical connection is a clamp connection.

13. The assembly of claim 1 wherein the body is welded to the vessel.

14. The assembly of claim 1 wherein the body is bonded with the vessel.

15. The assembly of claim 1 wherein the body is a singular unit with the vessel.

16. The assembly of claim 1 wherein the one or more fluid transfer conduits comprises a thermoset.

17. The assembly of claim 16 wherein the thermoset comprises silicone.

18. The assembly of claim 17 wherein the silicone is selected from the group consisting of dimethyl silicone, methyl phenyl silicone, and diphenyl silicone.

19. The assembly of claim 1 wherein the one or more fluid transfer conduits comprises a thermoplastic.

20. The assembly of claim 1 wherein the one or more fluid transfer conduits extend from the interior of the vessel through the fluid transfer interface to the exterior of the vessel.

21. The assembly of claim 1 wherein one or more anchors secure the one or more fluid transfer conduits to the body.

* * * * *